US011207198B2

United States Patent
Oh et al.

(10) Patent No.: US 11,207,198 B2
(45) Date of Patent: Dec. 28, 2021

(54) DETACHABLE KNEE TRIAL

(71) Applicant: CORENTEC CO., LTD., Chungcheongnam-do (KR)

(72) Inventors: Seung-Hun Oh, Seoul (KR); Chan-Eol Kim, Seoul (KR); Seok-Joo Kim, Seoul (KR); Oui-Sik Yoo, Seoul (KR)

(73) Assignee: Corentec Co., Ltd., Chungcheongnam-do (KR)

( * ) Notice: Subject to any disclaimer, the term of this patent is extended or adjusted under 35 U.S.C. 154(b) by 140 days.

(21) Appl. No.: 16/494,655

(22) PCT Filed: Mar. 19, 2018

(86) PCT No.: PCT/KR2018/003180
§ 371 (c)(1),
(2) Date: Sep. 16, 2019

(87) PCT Pub. No.: WO2018/174497
PCT Pub. Date: Sep. 27, 2018

(65) Prior Publication Data
US 2020/0008959 A1  Jan. 9, 2020

(30) Foreign Application Priority Data
Mar. 23, 2017 (KR) .......................... 10-2017-0036946

(51) Int. Cl.
*A61F 2/38* (2006.01)
*A61F 2/46* (2006.01)

(52) U.S. Cl.
CPC .......... *A61F 2/4684* (2013.01); *A61F 2/3836* (2013.01); *A61F 2/4637* (2013.01)

(58) Field of Classification Search
CPC .................................................. A61F 2/4684
See application file for complete search history.

(56) References Cited

U.S. PATENT DOCUMENTS 5,108,442 A * 4/1992 Smith ..................... A61F 2/389
623/20.33
6,004,352 A * 12/1999 Buni ..................... A61F 2/3886
623/20.33

(Continued)

FOREIGN PATENT DOCUMENTS

KR  10-2015-0096186 A  8/2015

OTHER PUBLICATIONS

International Search Report dated Aug. 13, 2018, issued in PCT Application No. PCT/KR2018/003180, filed Mar. 19, 2018.

(Continued)

*Primary Examiner* — Nicholas W Woodall
(74) *Attorney, Agent, or Firm* — Workman Nydegger

(57) ABSTRACT

A knee trial which is coupled to identify the mobility of an implant before the implant is implanted by total knee arthroplasty, and more particularly, a detachable knee trial which includes a plate trial, an insert trial, and an adapter for easy attachment and detachment of the two trials, wherein the adapter includes an elastic member on one side thereof to firmly couple the two trials by pressing the plate trial and the insert trial with opposite ends of the elastic member and to alleviate the burdens of an operator and a patient by allowing the adapter to be attached and detached even only with a simple operation of pressing the adapter and compressing the elastic member by a hand and promptly and precisely performing an operation of selecting an implant of a suitable size while applying various trials in the total knee arthroplasty process and shortening surgery time, alleviating the burdens of a surgeon and a patient, and wherein one side of the adapter is formed of plastic, making it possible to couple the plate trial and the plate implant without leaving a flaw and the like in the plate trial and the plate implant.

9 Claims, 16 Drawing Sheets

(56) References Cited

U.S. PATENT DOCUMENTS

| | | | | |
|---|---|---|---|---|
| 6,126,692 | A * | 10/2000 | Robie | A61F 2/389 |
| | | | | 623/20.32 |
| 7,175,660 | B2 * | 2/2007 | Cartledge | A61B 17/00234 |
| | | | | 623/2.11 |
| 8,617,250 | B2 * | 12/2013 | Metzger | A61F 2/389 |
| | | | | 623/20.32 |
| 8,740,984 | B2 * | 6/2014 | Hartdegen | A61F 2/389 |
| | | | | 623/20.32 |
| 10,258,477 | B2 * | 4/2019 | Jordan | A61F 2/3868 |
| 10,675,153 | B2 * | 6/2020 | Byrd | A61F 2/389 |
| 2005/0075736 | A1 | 4/2005 | Collazo | |
| 2009/0125114 | A1 | 5/2009 | May | |
| 2011/0066248 | A1 * | 3/2011 | Ries | A61F 2/4684 |
| | | | | 623/20.32 |
| 2012/0158152 | A1 | 6/2012 | Claypool | |
| 2014/0364956 | A1 | 12/2014 | Smith | |

OTHER PUBLICATIONS

Written Opinion dated Aug. 13, 2018, issued in PCT Application No. PCT/KR2018/003180, filed Mar. 19, 2018.

* cited by examiner

DETACHABLE KNEE TRIAL

BACKGROUND OF THE INVENTION

1. Field of the Invention

The present disclosure relates to a knee trial which is coupled to identify the mobility of an implant before the implant is implanted according to total knee arthroplasty, and more particularly, to a detachable knee trial which includes a plate trial, an insert trial, and an adapter for easy attachment and detachment of the two trials, wherein the adapter includes an elastic member on one side thereof, opposite ends of which press the plate trial and the insert trial, respectively, to firmly couple the two trials, so that the adapter can be attached or detached by a simple operation of pressing the adapter by a hand to compress the elastic member. Therefore, the present disclosure enables rapid and exact execution of an operation of selecting an implant of a suitable size while applying various trials in the total knee arthroplasty process, and thus shortens surgery time to alleviate the burdens of an operator and a patient. Further, the present disclosure relates to a knee trial, wherein one side of the adapter is formed of plastic, making it possible to couple the plate trial and the plate implant without leaving a scratch, etc. in the plate trial and the plate implant.

2. Description of the Prior Art

A patella is a joint portion that connects a tibia and a femur, and total knee arthroplasty of implanting an implant capable of replacing a joint when the joint loses its function due to wear or an injury is conducted.

The knee arthroplasty is a complex process that requires a high level of surgical capacity, and the implant used for the process may mainly include a tibia insertion member, a femur insertion member, and an insert that is located between the tibia insertion member and the femur insertion member to function as a bearing. A method for conducting total knee arthroplasty will be described with reference to the following document.

PATENT DOCUMENTS

Korean Patent No. 10-0901528 (published on Jun. 8, 2009) entitled 'Artificial Patella for Preventing Damage to Ligament')

As illustrated in the patent document, after surgical portions are formed in a femur and a tibia, a femur coupling member is implanted in a femur and a tibia coupling member provided with a baseplate at an upper portion thereof is implanted in the tibia. Next, an insert that functions as a bearing is attached to an upper side of the baseplate of the tibia coupling member to facilitate a smooth motion of the femur coupling member.

However, implants of various sizes are required because the locations and sizes of the tibia, the femur, and the patella are slightly different for each patient, and it is difficult to accurately recognize, among the implants of various sizes, which implant is suitable for the corresponding patient before the implant is directly attached and the mobility of the implant is tested. Accordingly, a process of temporarily attaching a trial (a test part) having a shape similar to that of an implant and testing the mobility of the implant, so as to select a size optimal to a corresponding patient is essentially required before the implant is implanted. This process requires trials of various sizes and thus requires much time.

In the conventional knee trial, the temporary attachment of the plate trial P and the insert trial A is not firm, and in particular, when an insert trial of 12 to 14 mm is used, the insert trial may be separated from the plate trial. In this case, the mobility of the knee cannot be precisely evaluated, and implantation of such an inaccurate implant may have a bad influence on the health of the patient. Further, when the surgery time increases for precise evaluation in such an unstable coupling state, the surgery time may increase, burdening the patient.

Further, as in FIGS. 1 and 2, grooves may be formed on sides of the two trials and bolts B or rods R may be inserted into the grooves to fix the trials. However, in this case, the attachment process requires excessive force and too much time, thereby burdening the surgeon. Further, the process of removing an already attached trial to try attaching a trial of another size is also complex and troublesome, and thus requires longer surgery time and may resultantly have a bad influence on the recovery of the health of the patent after the surgical operation of the patient.

Accordingly, it is necessary to alleviate the burden of the surgeon by simplify the surgical process as much as possible, and for the health of the patient, a measure for a prompt and simple surgical operation by simplifying a process of attaching and detaching a trial is required.

SUMMARY OF THE INVENTION

The present disclosure has been made in order to solve the above-described problems, and provides a detachable knee trial wherein the knee trial, which is coupled in order to identify the mobility of an implant before the implant is implanted according to total knee arthroplasty, can be easily coupled or separated, and includes an adapter and an insert trial separately configured from each other to enable application of various insert trials through a single adapter.

The present disclosure also provides a detachable knee trial, which includes two trials elastically pressed and firmly coupled to each other, so that an operation of identifying the mobility of an implant can be easily and precisely carried out and a suitable implant can thus be effectively selected.

The present disclosure also provides a detachable knee trial, wherein coupling of two trials can be released promptly and easily by removing elastic pressing through a simple operation of pressing one side of an adapter by a hand, so that the burden of a surgeon is alleviated and surgery time is shortened, thus facilitating patient recovery.

The present disclosure also provides a detachable knee trial, wherein an adapter thereof includes a body part and a pressing part operatively coupled to each other, so that the two trials are elastically pressed to firmly maintain the coupling, making it possible to carry out an operation of identifying the mobility of an implant easily and precisely, whereby a suitable implant can be selected more effectively.

The present disclosure also provides a detachable knee trial, wherein an adapter is coupled to an insert trial in a sliding manner to enable more easy and prompt coupling and releasing of the two trials, so as to alleviate the burden of a surgeon and shorten the surgery time, thereby helping improvement of the health of the patient.

The present disclosure also provides a detachable knee trial, which includes a pressing part received in a body part to guide the direction of elastic compression, to enable convenient and prompt attachment or detachment, so as to alleviate the burden of a surgeon and shorten the surgery time, thereby helping improvement of the health of the patient, and includes an elastic member elastically supported by the body part and the pressing part to maintain firm coupling of two trials.

The present disclosure also provides a detachable knee trial, which includes a guided slot disposed on one side of a pressing pipe to prevent disassembling of an adapter when two trials are coupled or separated, and to guide the compression direction in a simple and easy manner, so as to alleviate the burden of a surgeon and shorten the surgery time, thereby helping improvement of the health of the patient.

The present disclosure also provides a detachable knee trial, which includes a front separation preventing boss and a separation preventing step to prevent separation of an insert trial, so that an operation of identifying the mobility of an implant can be carried out more easily and precisely by maintaining the coupling of the two trials more firmly, making it possible to select a suitable implant more effectively.

The present disclosure also provides a detachable knee trial, wherein one side of a front separation preventing boss is chamfered to allow an insert trial to be easily and promptly coupled to or released from a plate trial, so as to alleviate the burden of a surgeon and shorten the surgery time, thereby helping improvement of the health of the patient.

The present disclosure also provides a detachable knee trial, which includes a separation preventing boss and a separation preventing step provided on the rear surface to prevent separation of an insert trial, similarly to those provided on the front surface, so as to enable the coupling of the two trials to be more firmly maintained, thereby making it possible to more easily and precisely carry out an operation of identifying the mobility of an implant and select a suitable implant more effectively.

The present disclosure also provides a detachable knee trial, wherein a portion of an upper surface of an adapter is inclined inwards like an oblique line portion of an insert trial to prevent collision with a patella at the time of testing the mobility of an implant, so that a more suitable implant can be effectively selected.

The present disclosure also provides a detachable knee trial, wherein one side of an adapter is made from plastic to reduce the possibility of scratching of the plate trial. Specifically, another embodiment of the present disclosure provides a detachable knee trial, which does not leave a scratch in a plate implant even after being subjected to a mobility test in a state where the detachable knee trial is coupled to the plate implant.

The present disclosure also provides a detachable knee trial, which includes a body part divided into a first body part and a second body part to allow the two body parts to be made of different materials, so as to diversify selectable materials, enable an optimum design, and enhance the durability, thereby increasing the life span of the knee trial.

The present disclosure also provides a detachable knee trial, wherein a second body part side of an adapter is made from plastic to reduce the possibility of scratching of the plate trial. Specifically, another embodiment of the present disclosure provides a detachable knee trial, which does not leave a scratch in a plate implant even after being subjected to a mobility test in a state where the detachable knee trial is coupled to the plate implant.

The present disclosure is realized by the embodiments having the following configurations in view of the foregoing.

According to an aspect of the present disclosure, a knee trial that is coupled to identify the mobility of an implant before the implant is implanted according to total knee arthroplasty includes a plate trial, an insert trial, and an adapter for attaching and detaching the plate trial and the insert trial, wherein the adapter easily couples and separates the plate trial and the insert trial.

According to another embodiment, the adapter may firmly couple the plate trial and the insert trial by elastically pressing the plate trial and the insert trial.

According to another embodiment, the coupling of the plate trial and the insert trial may be easily released by applying a pressure to one side of the adapter and removing the elastic pressing.

According to another embodiment, the adapter may include a pressing part including a body part and an elastic member, and the body part and the pressing part may be coupled to each other to be movable with respect to each other such that the adapter is elastically pressed or restored by the elastic member.

According to another embodiment, the body part may include a wing that is slid and guided with respect to the insert trial such that the adapter is slid with respect to the insert trial.

According to another embodiment, the pressing part may further include a pressing pipe having an insertion hole, in which the elastic member is accommodated, and one end of the elastic member may be elastically supported by the body part and an opposite end of the elastic member is elastically supported by the pressing pipe.

According to another embodiment, the pressing pipe may include a slot that is guided by the body part to be movable while being elastically pressed or restored in a forward/rearward direction in a state in which the pressing pipe is coupled to the body part.

According to another embodiment, the body part of the adapter may include a front separation preventing boss for firm coupling to the plate trial, on one side thereof, and the plate trial includes a front separation preventing step contacting the front separation preventing boss of the adapter, on one side thereof, such that the adapter is prevented from being separated from the plate trial.

According to another embodiment, one side of the front separation preventing boss may be chamfered to be easily coupled and released when being attached to and detached from the plate trial.

According to another embodiment, the insert trial may include a rear separation preventing boss for firm coupling to the plate trial, on a rear surface thereof, and the plate trial may include a rear separation preventing step contacting the separation preventing boss of the insert trial, on a rear surface thereof such that the insert trial is firmly coupled to the plate trial and is prevented from being separated.

According to another embodiment, an upper end of a front surface of the body part, which contacts the insert trial, may be chamfered inwards to have an inclination that is similar to an oblique line portion of the insert trial.

According to another embodiment, at least a portion of a contact surface of the body part of the adapter, which contacts the plate trial, may be formed of plastic such that the body part is attached and detached without leaving a scratch in the plate trial.

According to another embodiment, the body part may include a first body part and a second body part, and the first body part and the second body part may be coupled by a fastening member.

According to another embodiment, the second body part may be formed of plastic.

According to another embodiment, the present disclosure can have the following effects through the embodiment and the configurations, the coupling, and the use relationship, which will be described below.

According to the present disclosure, a knee trial, which is coupled to identify the mobility of an implant before the implant used is implanted by total knee arthroplasty, can be easily coupled or separated. Further, the separately configured adapter and insert trial allow application of one adapter to various insert trials.

Further, according to the present disclosure, an operation of identifying the mobility of an implant can be easily and precisely carried out by elastically pressing two trials and firmly coupling the trials so that a suitable implant can be effectively selected.

Further, according to the present disclosure, coupling of two trials can be released promptly and easily by removing elastic pressing through a simple operation of pressing one side of an adapter by one hand so that the burden of a surgeon is alleviated and surgery time is shortened, helping the health of a patient.

Further, according to the present disclosure, the adapter divided into a body part and a pressing part, which are operatively coupled to each other, enable the two trials to be elastically pressed to firmly maintain the coupling, making it possible to carry out an operation of identifying the mobility of an implant easily and precisely, whereby a suitable implant can be selected more effectively.

Further, according to the present disclosure, an adapter is coupled to an insert trial in a sliding manner to enable more easy and prompt coupling and releasing of the two trials, so as to alleviate the burden of a surgeon and shorten the surgery time, thereby helping improvement of the health of the patient.

Further, according to the present disclosure, a pressing part is received in a body part to guide the direction of elastic compression, to enable convenient and prompt attachment or detachment, so as to alleviate the burden of a surgeon and shorten the surgery time, thereby helping improvement of the health of the patient, and includes an elastic member elastically supported by the body part and the pressing part to maintain firm coupling of two trials.

Further, according to the present disclosure, a guided slot is disposed on one side of a pressing pipe to prevent disassembling of an adapter when two trials are coupled or separated, and to guide the compression direction in a simple and easy manner, so as to alleviate the burden of a surgeon and shorten the surgery time, thereby helping improvement of the health of the patient.

Further, according to the present disclosure, a front separation preventing boss and a separation preventing step prevent separation of an insert trial, so that an operation of identifying the mobility of an implant can be carried out more easily and precisely by maintaining the coupling of the two trials more firmly, making it possible to select a suitable implant more effectively.

Further, according to the present disclosure, one side of a front separation preventing boss is chamfered to allow an insert trial to be easily and promptly coupled to or released from a plate trial, so as to alleviate the burden of a surgeon and shorten the surgery time, thereby helping improvement of the health of the patient.

Further, according to the present disclosure, a separation preventing boss and a separation preventing step provided on the rear surface prevent separation of an insert trial, similarly to those provided on the front surface, so as to enable the coupling of the two trials to be more firmly maintained, thereby making it possible to more easily and precisely carry out an operation of identifying the mobility of an implant and select a suitable implant more effectively.

Further, according to the present disclosure, a portion of an upper surface of an adapter is inclined inwards like an oblique line portion of an insert trial to prevent collision with a patella at the time of testing the mobility of an implant, so that a more suitable implant can be effectively selected.

Further, according to the present disclosure, one side of an adapter is made from plastic to reduce the possibility of scratching of the plate trial. Specifically, another embodiment of the present disclosure provides a detachable knee trial, which does not leave a scratch in a plate implant even after being subjected to a mobility test in a state where the detachable knee trial is coupled to the plate implant.

Further, according to the present disclosure, a body part is divided into a first body part and a second body part to allow the two body parts to be made of different materials, so as to diversify selectable materials, enable an optimum design, and enhance the durability, thereby increasing the life span of the knee trial.

Further, according to the present disclosure, a second body part side of an adapter is made from plastic to reduce the possibility of scratching of the plate trial. Specifically, another embodiment of the present disclosure provides a detachable knee trial, which does not leave a scratch in a plate implant even after being subjected to a mobility test in a state where the detachable knee trial is coupled to the plate implant.

BRIEF DESCRIPTION OF THE DRAWINGS

The above and other aspects, features and advantages of the present disclosure will be more apparent from the following detailed description taken in conjunction with the accompanying drawings, in which.

DETAILED DESCRIPTION OF THE EXEMPLARY EMBODIMENTS

Figure 1:
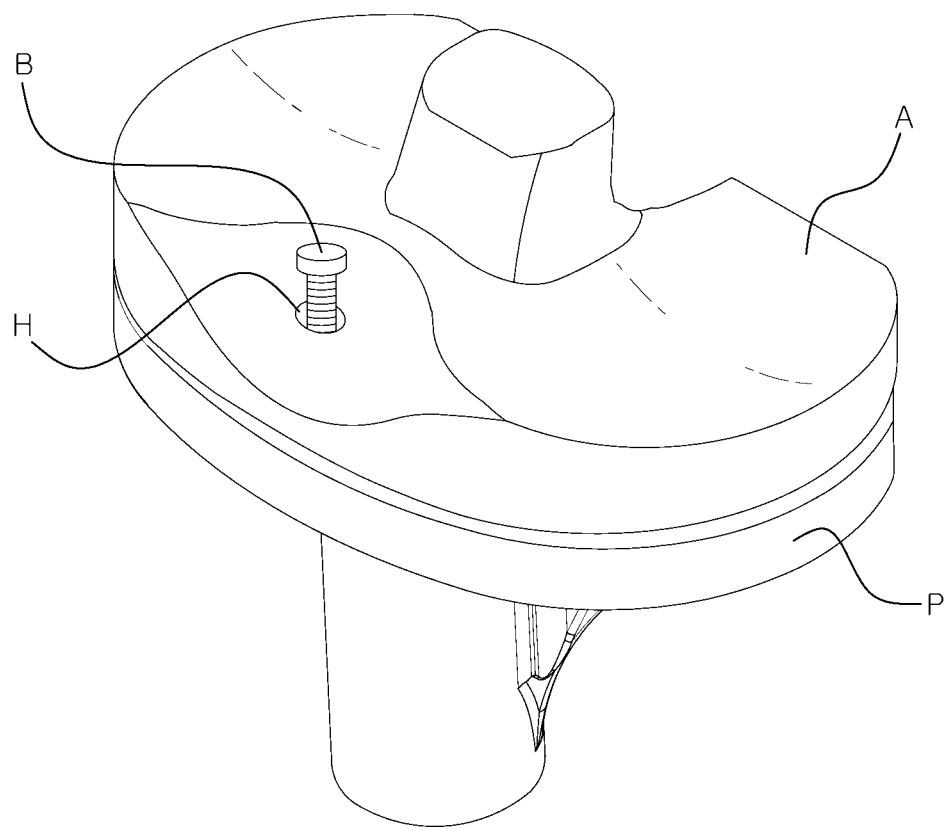
FIG. 1 is a perspective view illustrating a knee trial and a fixing device thereof according to the related art.

Hereinafter, a detachable knee trial according to the present disclosure will be described in detail with reference to the accompanying drawings. It is noted that the same elements are denoted by the same reference symbols anywhere in the drawings. Further, a detailed description of the known functions and configurations that may make the essence of the present disclosure unclear will be omitted. All the terms of the specification are the same as the general meanings of the terms, which are understood by an ordinary person in the art to which the present disclosure pertains, and if the terms used in the specification do not agree with the general meanings of the terms, their meanings follow the definitions used in the specification.

Then, the detachable knee trial of the present disclosure will be described in detail with reference to the drawings.

Figure 2:
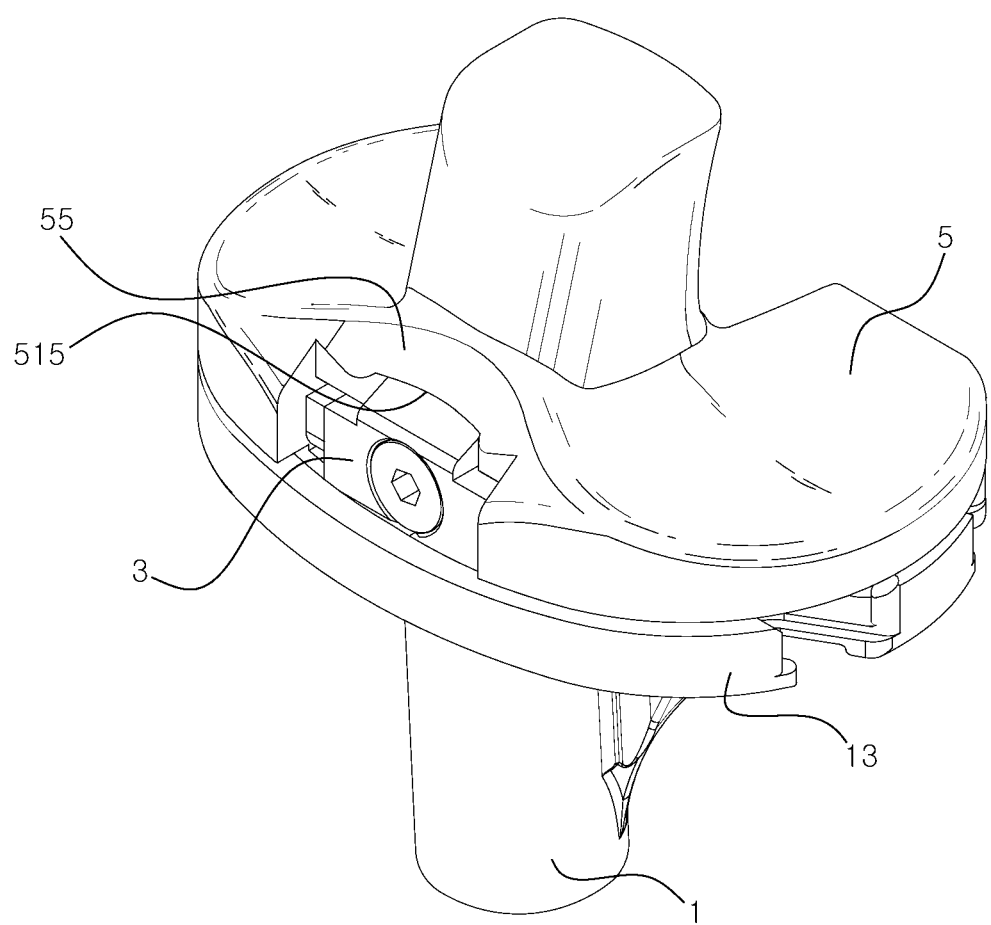
FIG. 2 is a perspective view illustrating a coupling state of a knee trial according to an embodiment of the present disclosure.
Figure 3:
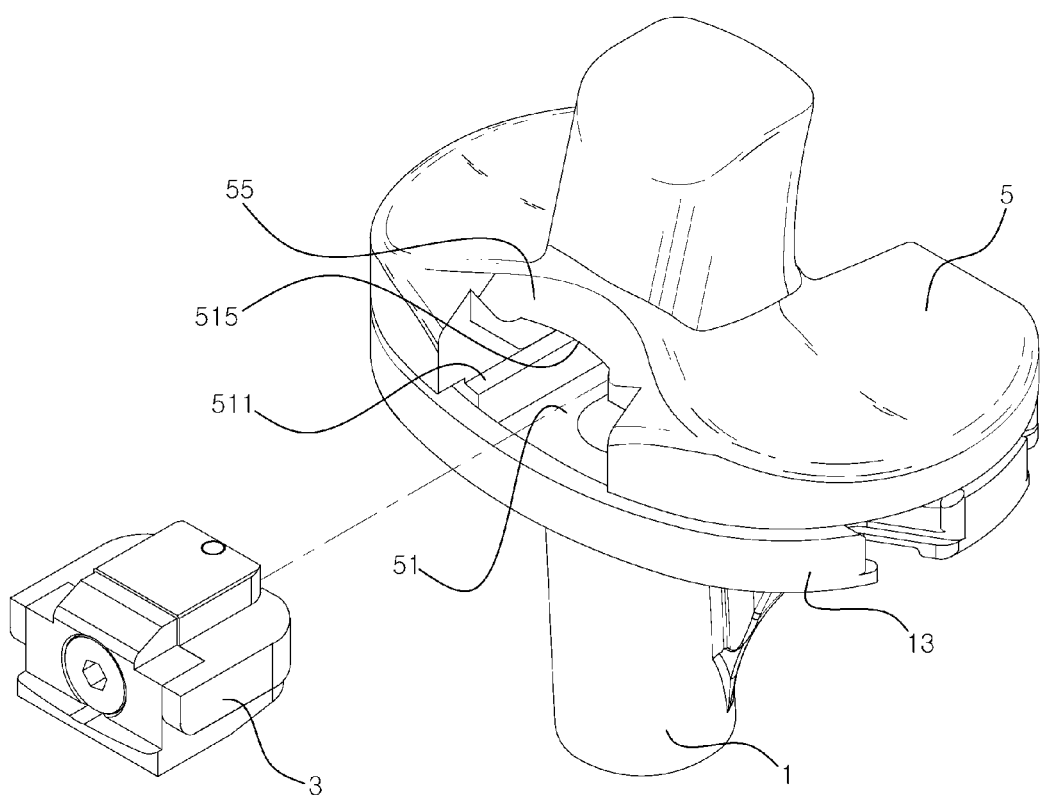
FIG. 3 is a perspective view illustrating a disassembled state of an adapter of the knee trial, an insert, and a plate trial according to the embodiment of the present disclosure.
Figure 4:
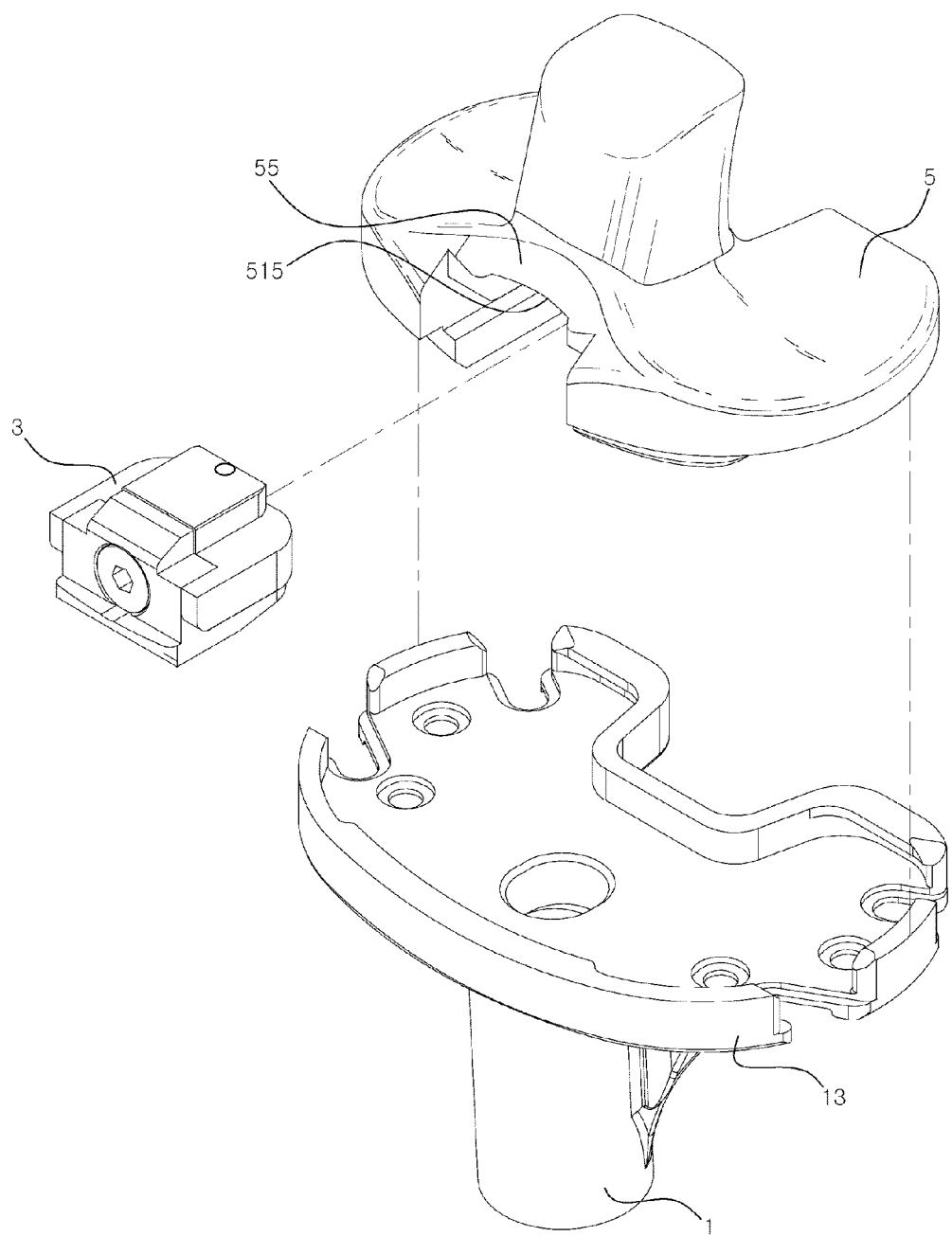
FIG. 4 is a perspective view illustrating an exploded state of the knee trial according to the embodiment of the present disclosure.
Figure 5:
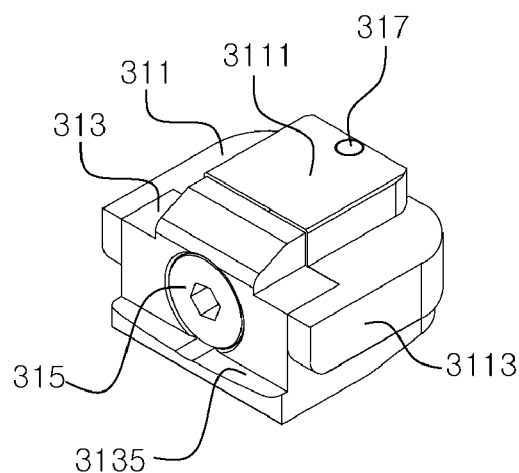
FIG. 5 is a perspective view of the adapter according to the embodiment of the present disclosure.
Figure 6:
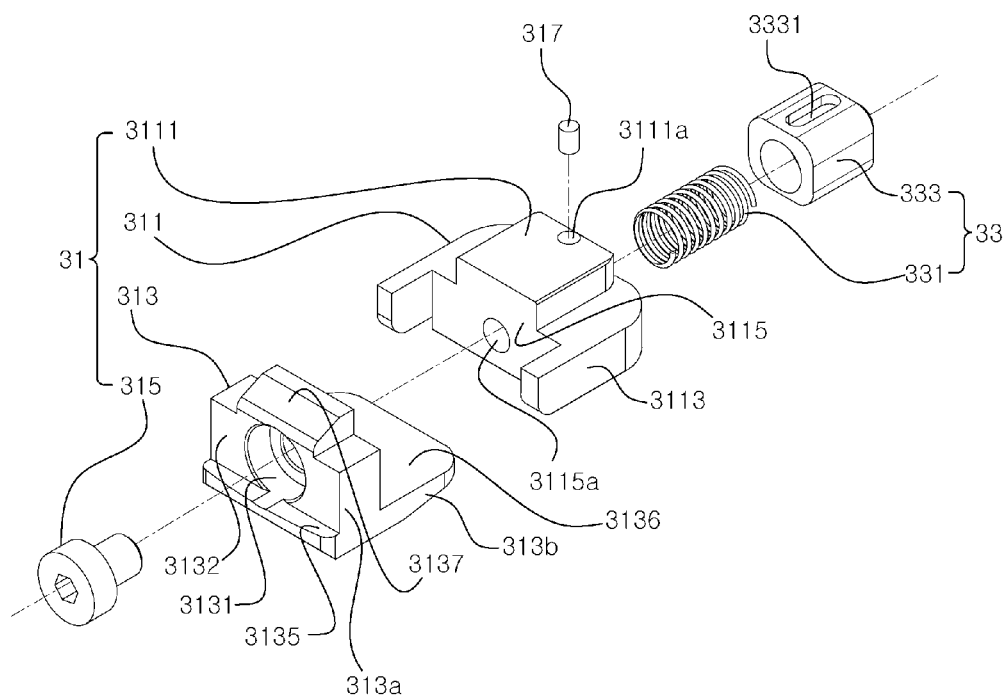
FIG. 6 is an exploded perspective view of the adapter according to the embodiment of the present disclosure.
Figure 7:
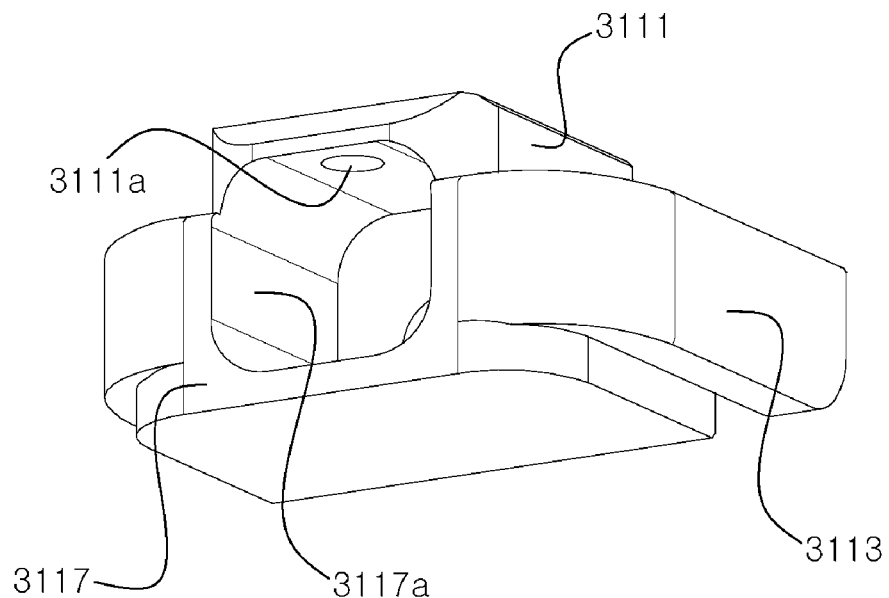
FIG. 7 is a perspective view of a first body of the adapter according to the embodiment of the present disclosure.
Figure 8:
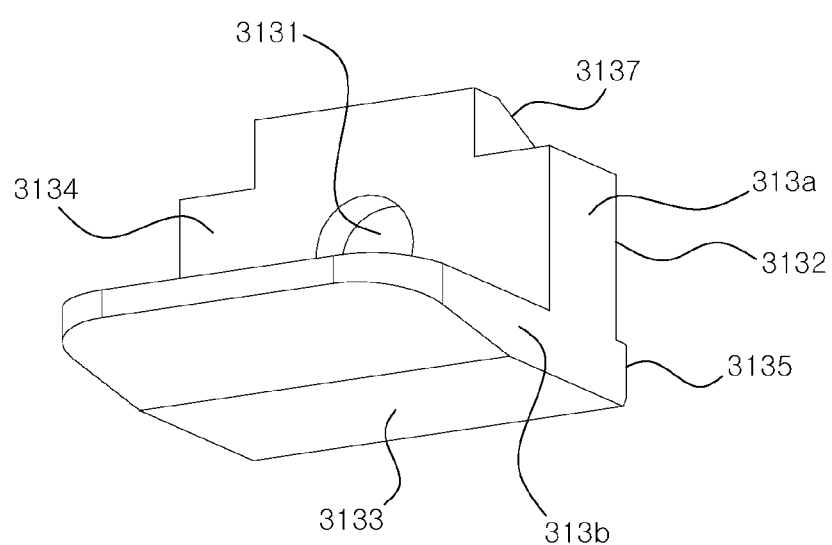
FIG. 8 is a perspective view of a second body of the adapter according to the embodiment of the present disclosure.
Figure 9:
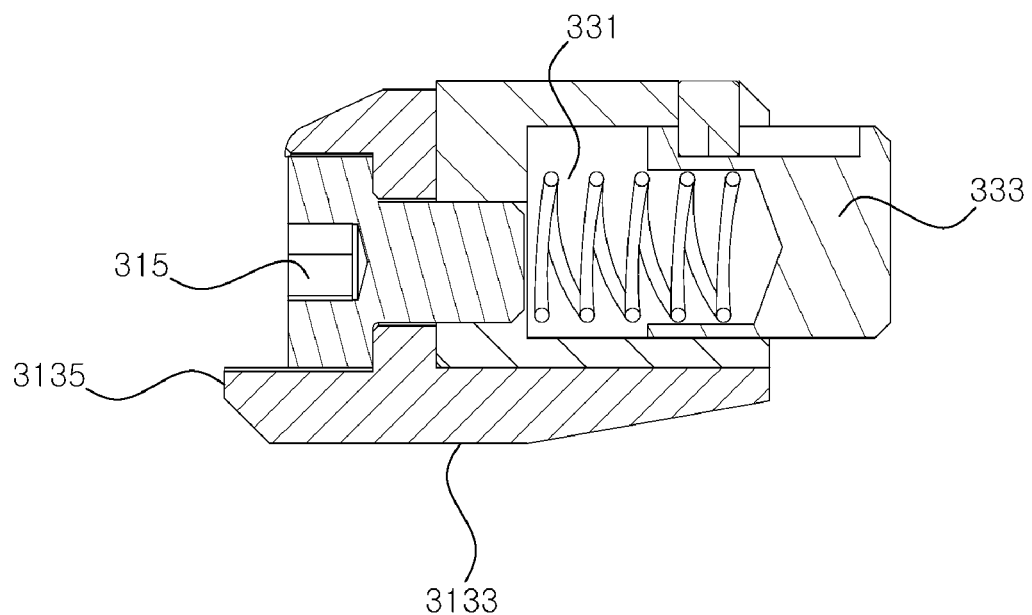
FIG. 9 is a side sectional view of the adapter according to the embodiment of the present disclosure.
Figure 10:
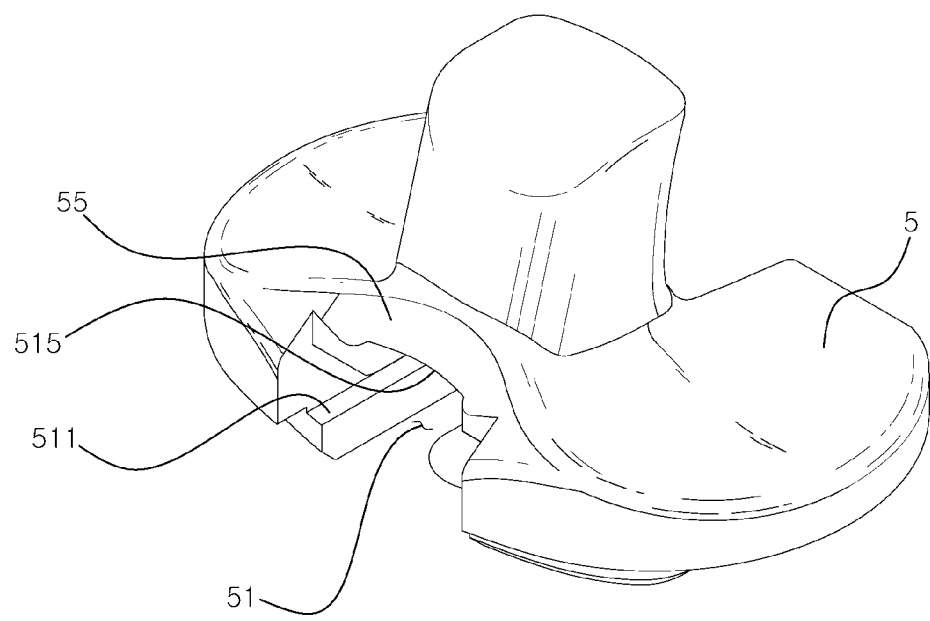
FIG. 10 is a perspective view of the insert trial according to the embodiment of the present disclosure.
Figure 11:
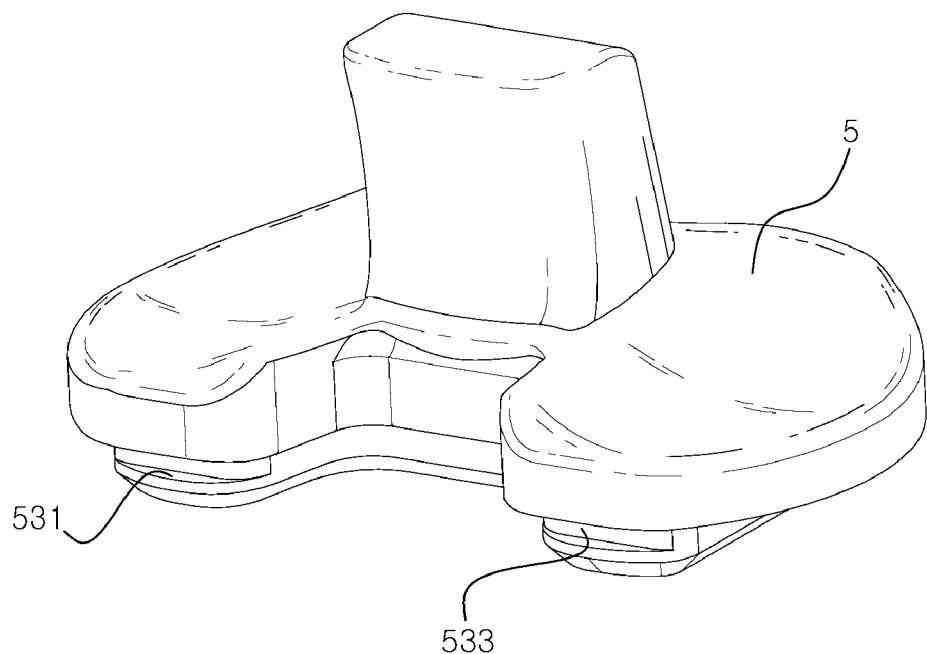
FIG. 11 is a rear perspective view of the insert trial according to the embodiment of the present disclosure.
Figure 12:
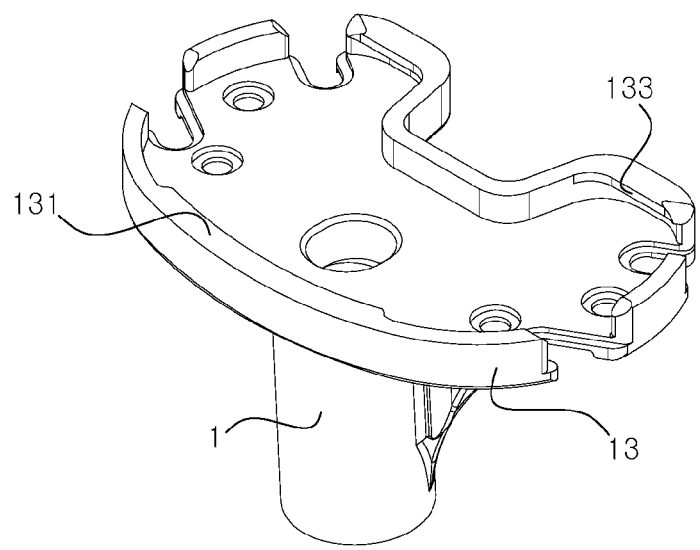
FIG. 12 is a perspective view of the plate trial according to the embodiment of the present disclosure.
Figure 13:
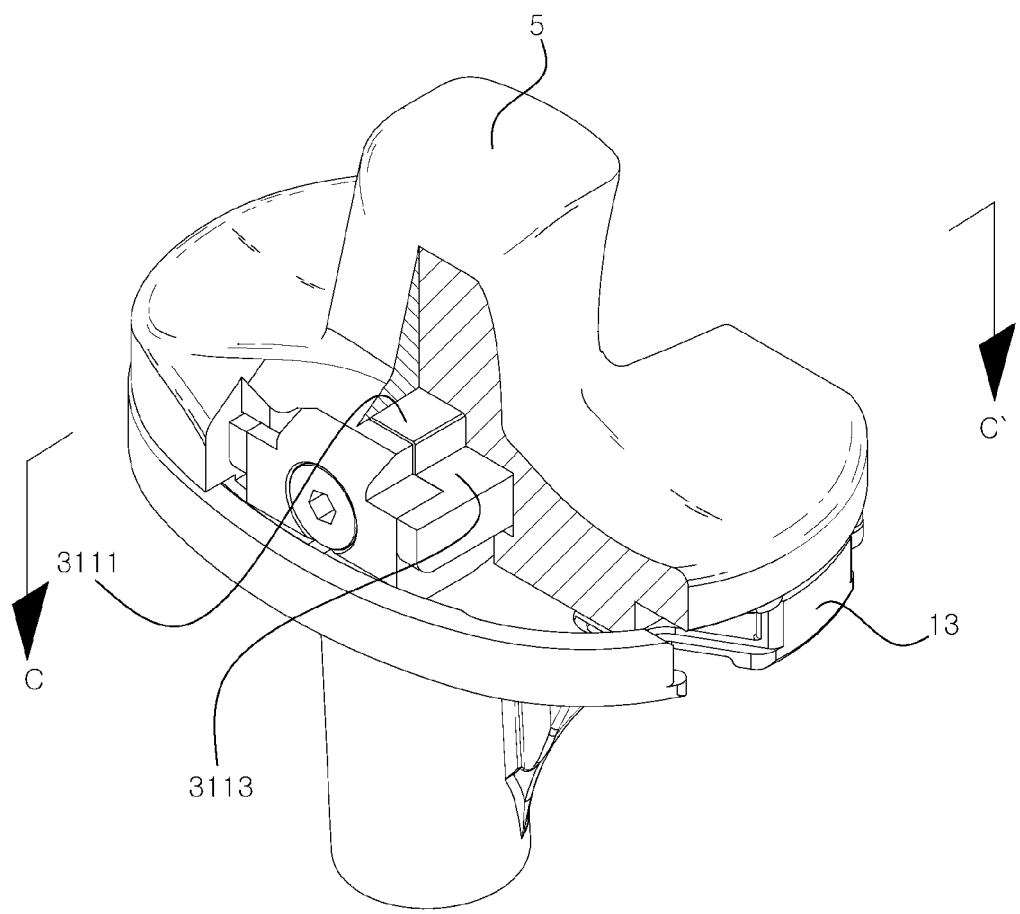
FIG. 13 is a partially cutaway perspective view illustrating a coupling state of the knee trial according to the embodiment of the present disclosure.
Figure 14:
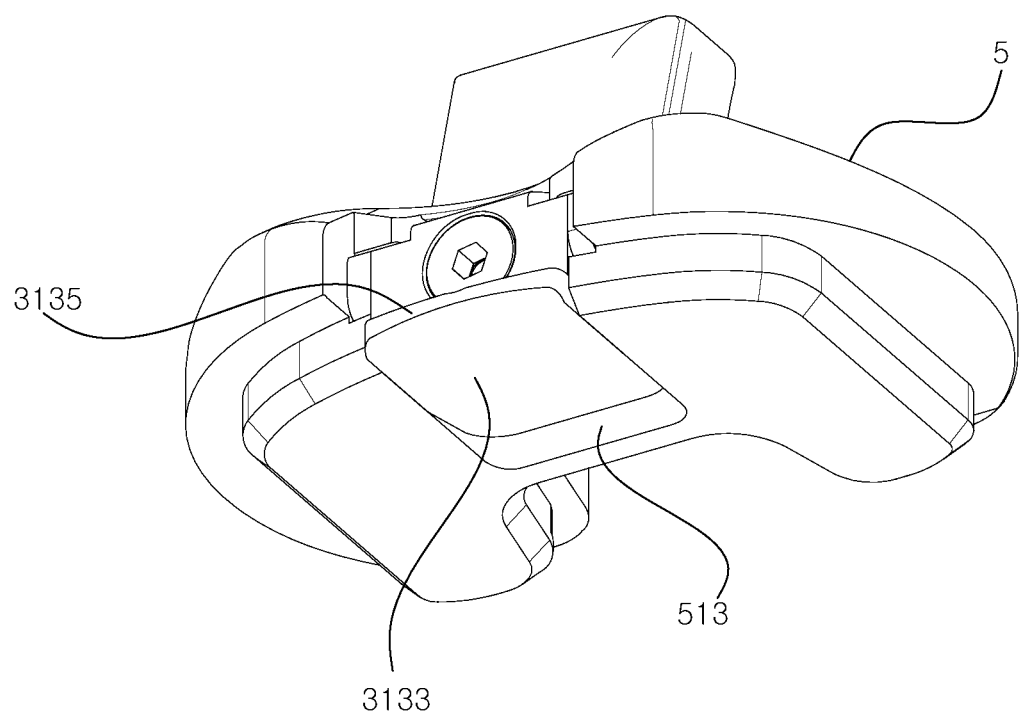
FIG. 14 is a partially coupled bottom perspective view illustrated a state in which only the insert trial and the adapter are coupled to each other according to the embodiment of the present disclosure, viewed from the bottom.
Figure 15:
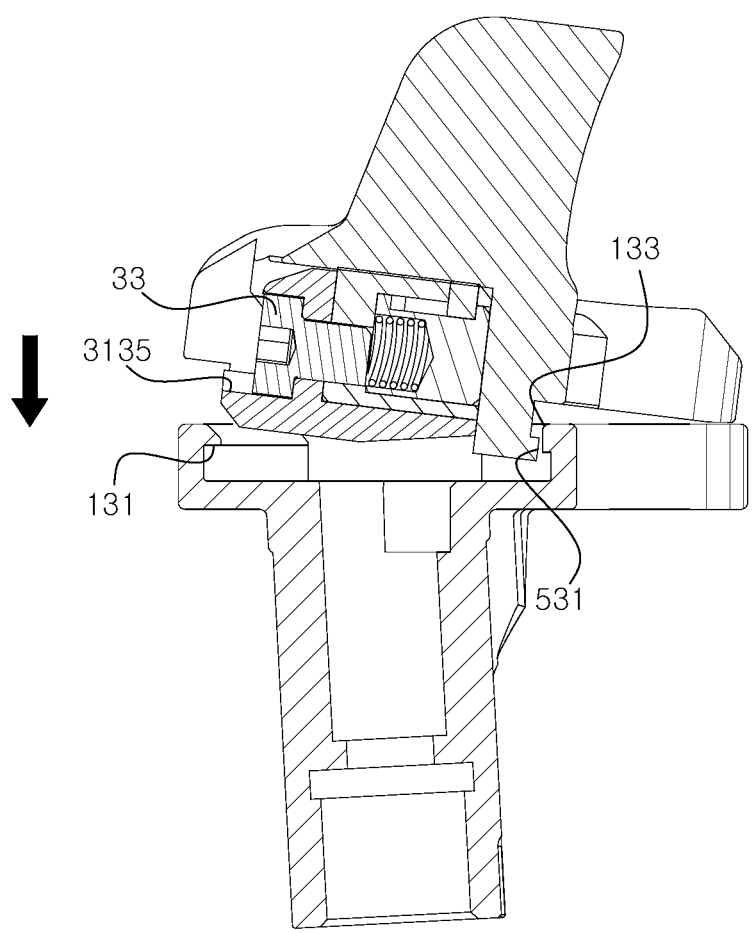
FIG. 15 is a cross-sectional view taken along line C-C', illustrating a preparation process for attaching the insert trial to the plate trial by pressing the adapter and the insert trial downwards according to the embodiment of the present disclosure.
Figure 16:
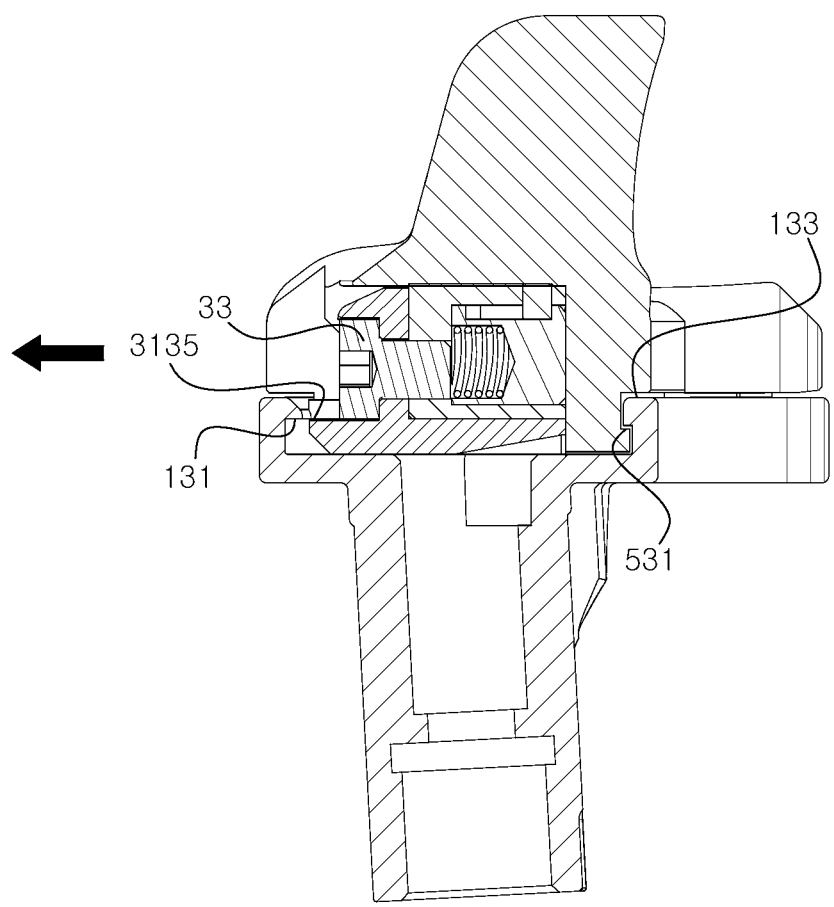
FIG. 16 is a cross-sectional view taken along line C-C', illustrating a process of coupling the insert trial to the plate trial by removing a force applied to one side of the adapter for compression of an elastic member according to the embodiment of the present disclosure.
Figure 17:
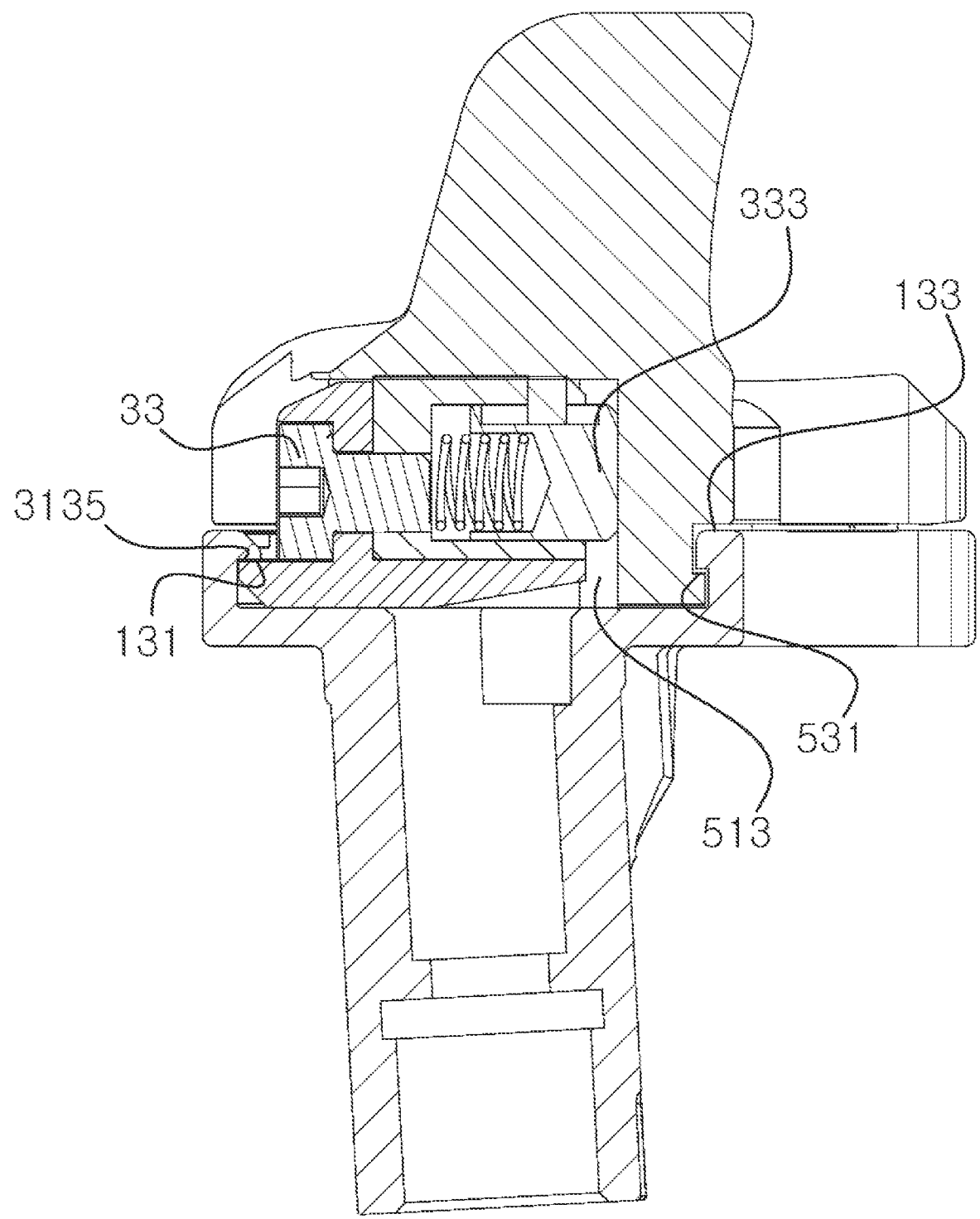
FIG. 17 is a cross-sectional view taken along line C-C', illustrating that the insert trial is coupled to the plate trial according to the embodiment of the present disclosure.
Figure 18:
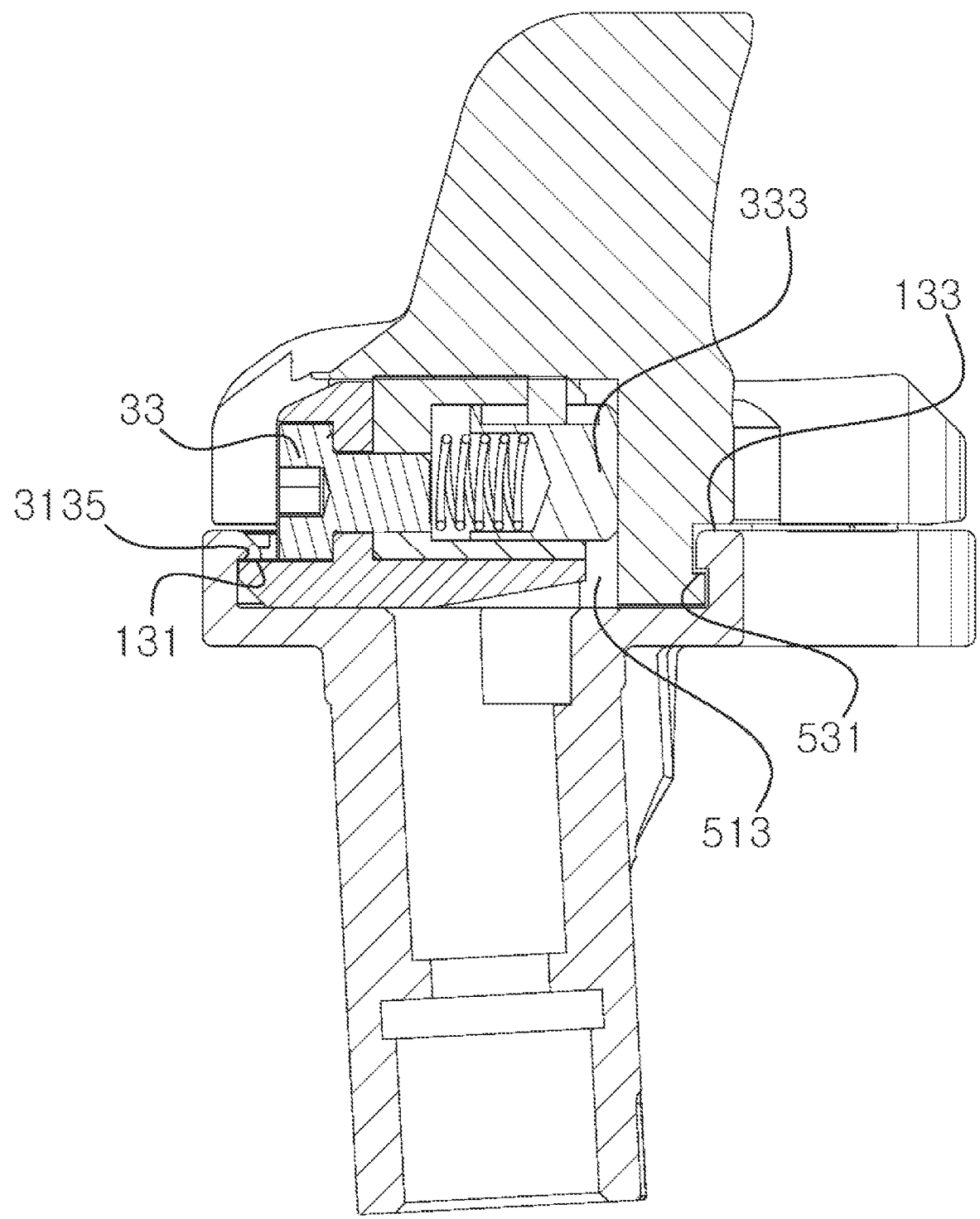
FIG. 18 is a cross-sectional view taken along line C-C', illustrating that the insert trial is coupled to the plate trial by the adapter according to the embodiment of the present disclosure.
Figure 19:
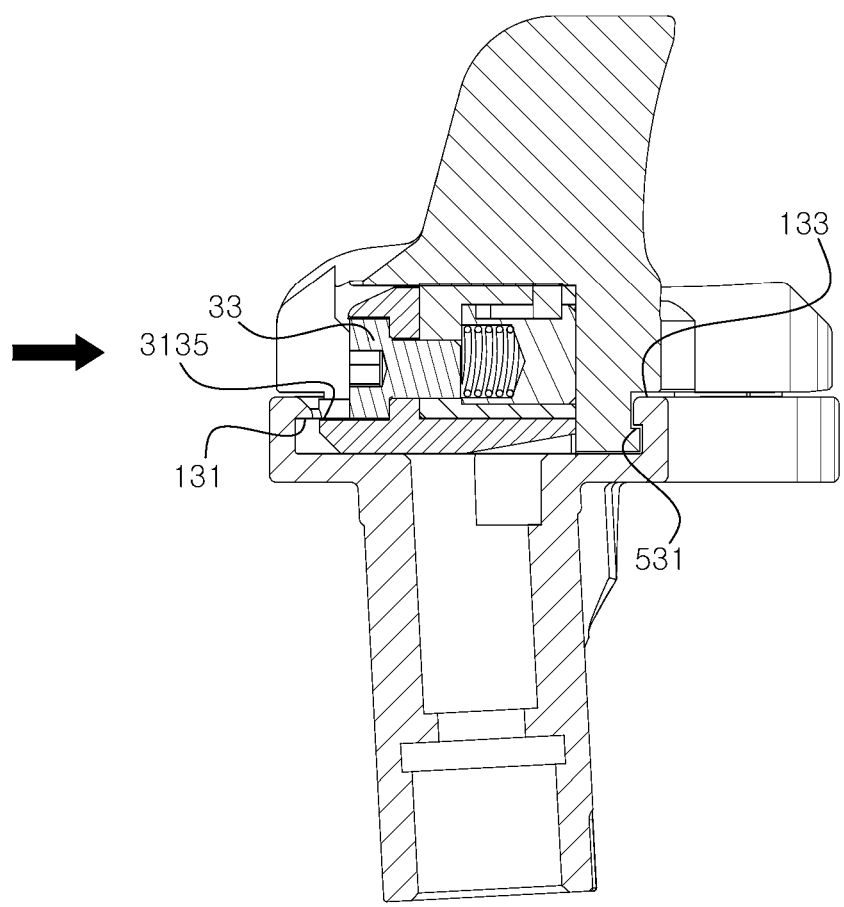
FIG. 19 is a cross-sectional view taken along line C-C', illustrating a preparation process for removing the insert trial from the plate trial by pressing one side surface of the adapter according to the embodiment of the present disclosure.
Figure 20:
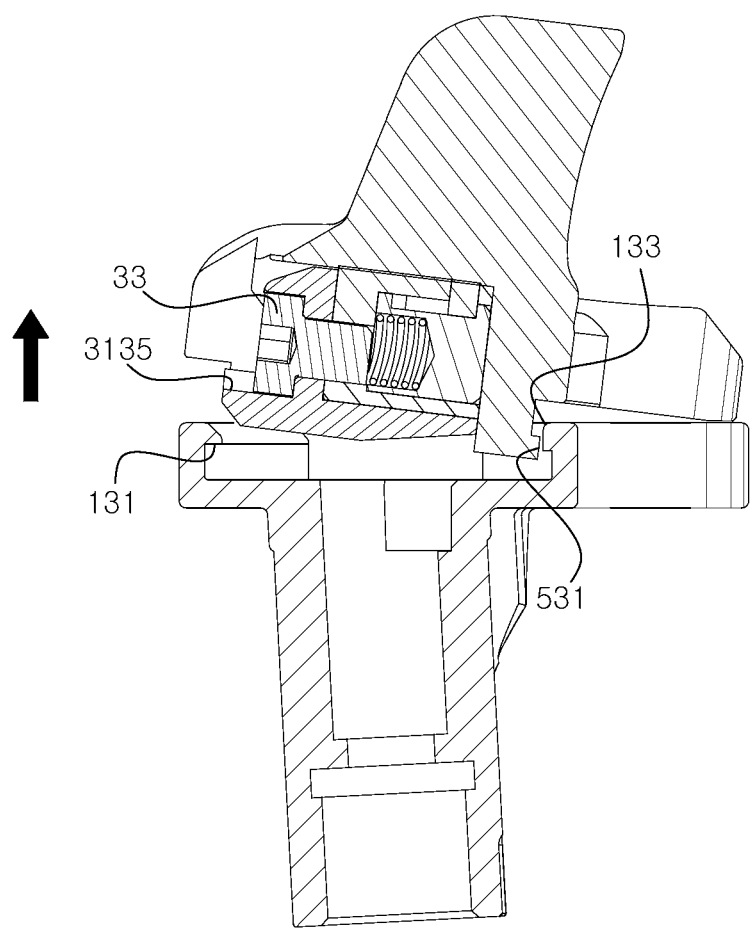
FIG. 20 is a cross-sectional view taken along line C-C', illustrating that the insert trial is removed from the plate trial by lifting the adapter and the insert trial upwards according to the embodiment of the present disclosure.

FIG. 1 is a perspective view of an insert trial and a plate trial having a bolt fixing device according to the related art. FIG. 2 is a perspective view illustrating a coupled state of an insert trial, a plate trial, and an adapter according to an embodiment of the present disclosure. FIG. 3 is a partially exploded perspective view of the two trials and the adapter according to the embodiment of the present disclosure. FIG. 4 is a completely exploded perspective view according to the embodiment of the present disclosure. FIG. 5 is a perspective view of the adapter according to the embodiment of the present disclosure. FIG. 6 is an exploded perspective view of the adapter according to the embodiment of the present disclosure. FIG. 7 is a perspective view of a first body according to the embodiment of the present disclosure. FIG. 8 is a perspective view of a second body according to the embodiment of the present disclosure. FIG. 9 is a side sectional view of the adapter according to the embodiment of the present disclosure. FIG. 10 is a front perspective view of the insert trial according to the embodiment of the present disclosure. FIG. 11 is a rear perspective view of the insert trial according to the embodiment of the present disclosure. FIG. 12 is a perspective view of the plate trial according to the embodiment of the present disclosure. FIG. 13 is a partially cutaway perspective view illustrating a coupling state of the knee trial according to the embodiment of the present disclosure. FIG. 14 is a partially coupled bottom perspective view illustrated a state in which only the insert trial and the adapter are coupled to each other according to the embodiment of the present disclosure, viewed from the bottom. FIG. 15 is a cross-sectional view taken along line C-C' illustrating a coupling preparation step of the two trials and the adapter according to the embodiment of the present disclosure. FIG. 16 is a cross-sectional view taken along line C-C' illustrating a coupling principle according to the embodiment of the present disclosure. FIG. 17 is a cross-sectional view taken along line C-C' illustrating a coupling state according to the embodiment of the present disclosure. FIG. 18 is a cross-sectional view taken along line C-C' illustrating a preparation step for a separation process according to the embodiment of the present disclosure. FIG. 19 is a cross-sectional view taken along line C-C' illustrating the separation process according to the embodiment of the present disclosure. FIG. 20 is a cross-sectional view taken along line C-C' illustrating a coupling completed state according to the embodiment of the present disclosure.

Referring to FIGS. 2, 3, and 4 illustrating the present disclosure, the knee trial of the present disclosure includes an insert trial 5, a plate trial 13 on a tibia coupling member 1, and an adapter 3. The insert trial 5 is located on the upper side of the plate trial 13 and the adapter 3 is located between the two trials 13 and 5, which can be identified from FIG. 3. Opposite sides of the adapter 3 elastically press the trials 5 and 13 for maintaining firm coupling. Accordingly, the adapter 3 functions to facilitate a more precise test when the mobility of the corresponding size is tested before coupling of an implant. Further, when attachment and detachment of the insert trial 5 and the plate trial 13 are tried to test a trial of a different size, the adapter 3 functions to facilitate easy attachment and detachment.

A configuration of the adapter 3 will be discussed in detail with reference to FIGS. 5 to 9.

Referring to FIGS. 5 and 6, the adapter 3 may include a body part 31 and a pressing part 33. The body part 31 is a part that is seated in an adapter accommodating part 51 of the insert trial 5 while defining the body of the adapter 3. Opposite ends of the pressing part 33 are supported by the body part 31 and the insert trial 5 to press the body part 31 and the insert trial 5, respectively. The body part 31 and the pressing part 33 are coupled to each other to be movable with respect to each other to attach and detach the knee trial.

The body part 31 may include a first body 311, a second body 313, a coupling unit 315, and a rod 317.

Referring to FIG. 7, the first body 311 may include a front portion 3115 that is a portion which is coupled to the second body 313 to contact the second body 313, an upper portion 3111 in which the rod 317 for preventing separation of the pressing part 33 is accommodated, a wing 3113 protruding to the outside for easy coupling and releasing to and from the insert trial 5, and a rear portion 3117 including an accommodation hole 3117a that accommodates the pressing part 33.

The front portion 3115 of the first body 311 is a portion that contacts the second body 313, and may include an insertion hole 3115a, into which the coupling unit 315 for coupling to the second body 313 is inserted to be located therein. The coupling unit 315 that passes through the second body 313 is seated in the insertion hole 3115a and fixes the coupling of the two bodies, which will be described in detail.

The upper portion 3111 of the first body 311 is a portion that protrudes upwards in a box form, and may accommodate the rod 317 functioning to grip the body part 31 and the pressing part 33 such that the body part 31 and the pressing part 33 do not deviate. In this case, a rod fixing hole 3111a for fixing the rod 317 may be included in the upper portion 3111. By the rod 317, the pressing part 33 can be prevented from deviating by a predetermined distance or more to be coupled operatively, which will be described later in detail.

Further, as the upper portion 3111 is narrower and higher than the wing 3113, the upper portion 3111 is inserted into or separated from an upper guide groove 515 located in the interior of the adapter accommodating part 51 of the insert trial 5, which will be described below, and is seated in the upper guide groove 515. Accordingly, the upper portion 3111 functions to facilitate prompt and convenient coupling and releasing of the adapter 3, as well as the wing.

The wing 3113 protrudes from a lower end of the upper portion leftwards and rightwards, and is coupled to be slid along a wing guide groove 511 of the adapter accommodating part 51 included in the insert trial 5, which will be described below. As the direction of the adapter 3 is constantly guided when the adapter 3 is inserted into the adapter accommodating part 51 of the insert trial 5 due to the wing 3113, the wing 3113 helps prompt and convenient attachment and detachment of the two trials 13 and 5.

Further, one side of the wing 3113 extends toward the second body 313, and may function to facilitate firm fixing by preventing the two bodies from deviating leftwards and rightwards when the two bodies are coupled.

The rear portion 3117 of the first body 311 is a portion that extends from one side of the upper portion 3111 downwards, and may include an accommodation hole 3117a that accommodates the pressing part 33. The accommodation hole 3117a is recessed to the inner side of the adapter 3 by a predetermined depth such that the pressing part 33 is accommodated in the accommodation hole 3117a, and it is preferable that the cross-section of the accommodation hole 3117a coincides with the cross-section of the pressing part 33. The accommodation hole 3117a surrounds a portion or the entire surface of the pressing part 33 such that the pressing part 33 is seated therein, and functions to guide the path of the pressing part 33 during pressing and releasing of the pressing part 33. As the pressing part 33 moves forwards and rearwards in the interior of the accommodation hole 3117a, the body part 31 and the pressing part 33 are operatively coupled to each other.

The first body 311 may use stainless steel for the durability thereof, but the present disclosure is not necessarily limited thereto and any material that does not obstruct attachment and detachment of the knee trial may be possible.

Referring to FIGS. 6 and 8, the second body 313 may include a front portion 313a that is exposed to the front side of the knee trial, and a lower portion 313b that supports the first body 311 from the lower side and contacts the plate trial 13.

The front portion 313a may include a front surface 3132 that is exposed to the front side, a rear surface 3134 contacting the first body 311, a through hole 3131 that passes through the front and rear surfaces of the front portion 313a and in which the coupling unit 315 is seated, an upper end 3137 that communicates with an oblique line portion 55 of the insert trial 5, and a front separation preventing boss 3135 that is coupled to a front separation preventing step 133 of the plate trial 13.

The front surface 3132 is a portion which is exposed to the front surface of the knee trial and to which a force is applied by a hand when the insert trial 5 is attached and detached to and from the plate trial 13.

The rear surface 3134 is located in a direction that is opposite to the front surface 3132 and contacts the first body 311.

The through hole 3131 is a hole in which the coupling unit 315 for firmly maintaining the coupling of the first body 311 and the second body 313 is seated, and passes through the front surface 3132 and the rear surface 3134. It is preferable that the cross-section of the through-hole 3131 coincides with the cross-section of the coupling unit 315.

The upper end 3137 may be chamfered to have an inclination like the oblique line portion 55 of the insert trial 5, and in this case, impingement of the knee trial with a patella can be prevented in a process of testing the mobility of the knee by using the knee trial. Moreover, when the adapter 3 is gripped by a hand in a process of pressing the adapter 3 for attachment and detachment, the adapter 3 is naturally connected to the oblique line portion 55 of the insert trial 5, allowing the adapter 3 to be gripped with a comfortable feeling.

The front separation preventing boss 3135 is provided on one side of the second body 313, and firmly maintains the coupling with the plate trial 13. In this case, a front separation preventing step 131 is provided on one side of the plate trial 13, which will be described below, and the coupling of the boss 3135 and the front separation preventing step 131 can become firmer by configuring the front separation preventing step 131 such that the front separation preventing step 131 contacts the boss 3135.

Further, in the case in which one side of the front separation preventing boss 3135 is chamfered, the boss 3135 enters and exits as if it was slid when being attached to and detached from the plate trial 13 so that they can be coupled and released promptly and conveniently. This can be understood more clearly with reference to the cross-sectional view of FIG. 9.

The lower portion 313b is a portion that extends flatly from a lower end of the front portion 313a rearwards, and may include an upper surface 3136 and a lower surface 3133.

The upper surface 3136 supports the first body 311 from the lower side in a direction in which the upper surface 3136 is opposite to the lower surface 3133.

The lower surface 3133 is a contact surface that contacts the plate trial 13, and may be formed of plastic. In this case, the lower surface 3133 may be coupled to the plate trial 13 without leaving a flaw and the like. The plastic may be POM-C, and may be any material that does not leave a flaw or the like. The part formed of plastic in this way may be limited to the lower surface 3133 that is the contact surface, and may be the entire part of the second body 313. Further, the configuration may be applied to the plate implant as well as the plate trial 13, which will be described in detail.

The coupling unit 315 is located in the insertion hole 3115a of the first body 311 and the through hole 3131 of the second body 313 and firmly maintains the coupling of the two bodies.

The coupling unit 315 may be a screw including a screw thread, and in this case, the insertion hole 3115a of the first body 311 and the through hole 3131 of the second body 313 include screw grooves. In addition, of course, any coupling unit 315 that couples the two bodies 311 and 313 is possible.

The rod 317 is fixed to the rod fixing hole 3111a located at the upper portion 3111 of the first body 311, and moves along the long axis of the slot 3331 of the pressing pipe 333, which will be described below, to operatively couple the body part 31 and the pressing part 33 and at the same time, prevents the body part 31 and the pressing part 33 from being separated. The rod 317 may have a cylindrical shape having a circular cross-section, may be a rectangular column having a rectangular cross-section, and may have any shape that prevents separation of the body part 31 and the pressing part 33 and allows the operative coupling.

Referring to FIG. 6, the pressing part 33 is a part that is operatively coupled to the body part 31, and may include an elastic member 331 and a pressing pipe 333 that surrounds the elastic member 331.

The elastic member 331 may be a spring or rubber, may be a cylinder that uses compressed air or various fluids or a closed tube, and additionally may be various members having elasticity. Due to the elastic member 331, the body part 31 presses the plate trial 13, and the pressing part 33 elastically couples the two trials 13 and 5 by pressing the insert trial 5.

The pressing pipe 333 may have a pipe shape, one side of which is opened, such that the elastic member 331 may be inserted into the interior of the pressing pipe 333, and in this case, the accommodation hole 3117a of the body part 31 surrounds the pressing pipe 333 while not directly surrounding the elastic member 331. It is preferable that the cross-section of the pressing pipe 333 has the same shape as the cross-section of the accommodation hole 3117a of the first body 311 such that the pressing pipe 333 may be naturally inserted as described above.

One side of the pressing pipe 333 may include a rod guide groove, in which the rod 317 may be located, in the form of a slot 3331. The rod 317 is fixed to the rod fixing hole 3111a of the upper portion 3111 of the first body 311 to move forwards and rearwards along the long axis of the slot 3331. The rod 317 operatively couples the body part 31 and the pressing part 33 through the movement scheme, and at the same time, controls the movement direction to one side. Further, the rod 317 closes opposite ends of the slot 3331, and thus may function to prevent separation of the body part 31 and the pressing part 33 if the rod 317 is gripped so as not deviate by a predetermined distance or more.

Next, the configurations of the insert trial 5 and the plate trial 13 will be described with reference to FIGS. 10, 11, and 12.

Referring to FIGS. 10 and 11, the insert trial 5 is a trial which has the same size as that of the insert implant that is to be implanted in a patient and is used for a test before the implanting of the implant, and may include an adapter accommodating part 51 on one side thereof, a rear adhering portion 53 coupled to the plate trial 13 on the rear side, and an oblique line portion 55.

The adapter accommodating part 51 is recessed inwards from the front side by a predetermined depth, and the adapter 3 is located in the space. The adapter accommodating part 51 may include a wing guide groove 511, an upper guide groove 515, and a compression space 513.

The wing guide groove 511 extends inwards from one side or opposite sides of the accommodation part 51, and the adapter 3 is simply and promptly inserted into and released from the insert trial 5 as the wing guide groove 511 guides the path of the wing 3113 of the adapter 3.

The upper guide groove 515 is located on the upper side of the wing guide groove 511, and may accommodate the upper portion 3111 of the first body 311 while guiding the upper portion 3111 in a predetermined direction when the adapter 3 is inserted into the upper guide groove 515.

The two guide grooves 511 and 515 constantly guide the directions of the wing 3113 and the upper portion 3111 when the adapter 3 is inserted and released, and perform a similar function in that they accommodate the adapter 3 while allowing a prompt and simple operation.

The compression space 513 is a space that is made empty such that the body part 31 including the pressing part 33, which is pushed in while contacting an end of the compression space 513, may be pushed rearwards when a force is applied to the adapter 3 to compress the elastic member 331. The compression space 513 is located on the rear side of the accommodation part 51, and the pressing part 33 transverses the compression space even before the compression and contacts the rear side of the compression space. It is preferable that the two guide grooves 511 and 515 extend to the compression space 513 to accommodate the wing 3113 and the upper portion 3111 when the elastic member 331 is compressed. This may be identified in FIG. 14, and the adapter 3 may be compressed and released in the interior of the insert trial 5 by the compression space 513.

Referring to FIG. 11, the rear adhering portion 53 is formed on a rear surface of the insert trial 5 to maintain firm coupling with the plate trial 13, and the coupling is maintained by a frictional force as the rear adhering surface 533 presses the plate trial 13 by the elastic pressing.

In this case, a rear separation preventing boss 531 is further provided, and a separation preventing step 133 is provided on a rear surface of the plate trial 13, which will be described below, to be contact each other and be hooked by each other, and thus firmer coupling can be maintained. Like the front boss 3135, one side of the rear separation preventing boss 531 is chamfered to be inserted and released as if it was slid when being attached to and detached from the plate trial 13 so that a prompt and simple surgery can be made.

The oblique line portion 55 is a portion that is chamfered centrally on an upper side of the upper guide groove 515. The oblique line portion 55 is a space in which a patella may be located when the mobility of the knee trial is tested, and has an effect of preventing collision with the patella. As described above, it is preferable that the oblique line portion 55 is chamfered to have an inclination as that of an upper end 3137 of the second body 313.

Referring to FIG. 12, the plate trial is a trial that has the same size as that of the plate implant that is to be implanted in a patient and is used for a test before the implant is implanted, and may include a front separation preventing step 131 and a rear separation preventing step 133.

The front separation preventing step 131 is a portion that protrudes inwards from a front surface of the plate trial 13 by a predetermined depth, and may contact the front separation preventing boss 3135 to maintain the coupling between them more firmly.

The rear separation preventing step 133 is a portion that protrudes inwards from the rear surface of the plate trial 13, and may contact the rear separation preventing boss 531 of the insert trial 5, which has been described above, to maintain the coupling between them more firmly and prevent separation of the insert trial 5 upwards, downwards, leftwards, and rightwards.

FIG. 13 is a partially cutaway perspective view illustrating a process of coupling the configurations such that the process can be easily understood, and it can be identified that the side wing 3113 of the adapter 3 is seated in the wing guide groove 511 of the insert trial 5. Further, it can be also seen that the upper portion 3111 of the adapter 3 is seated in the upper guide groove 515 of the insert trial 5. Through the configuration, the insert trial 5 and the plate trial 13 may be firmly coupled such that they are prevented from being shaken or separated.

It can be seen from FIG. 14 that only the adapter 3 and the insert trial 5 that are some configurations are coupled, and the compression space 513 that is an empty space is formed such that the pressing part 33 is seated in a normal state and enters the inside of the body part 31 when the elastic member 331 is compressed by applying a force to one side of the adapter 3.

The coupling principle of the knee trial will be described with reference to FIGS. 15, 16, and 17 on the basis of the described configuration. FIGS. 15, 16, and 17 are cross-sectional views taken along line C-C' of FIG. 13. The cutting line starting from C goes along the center of the insert trial 5, and goes along a side surface of the insert trial 5 from an intermediate point to C'. Actually, the rear separation preventing step of the adapter 3 and the bosses 133 and 531 are not on the same plane, but it is described for the purpose of describing the operation of the adapter 3 and the operations of the rear separation preventing step and the bosses 133 and 531 in the coupling process at once.

Referring to FIG. 15, the rear adhering portion 53 of the insert trial 5 is adhered to the plate trial 13 first. Then, the rear separation preventing boss 531 is coupled to the rear separation preventing step 133 for firm rear fixing. Next, the rear separation preventing boss 531 is pushed down in the direction of the arrow, and it is preferable that a force is applied to the front surface of the adapter 3 then. The body part 31 of the adapter 3 is pushed rearwards by the force, and there is no further retreatment space because the pressing part 33 already contacts an end of the inner side of the adapter accommodating part 51 of the insert trial 5. Consequently, the elastic member 331, opposite ends of which are supported by the first body 311 and the pressing pipe 333 is compressed by the Hooke's Law, and accordingly, the entire pressing part 33 enters the accommodation hole 3117a of the first body 311. In this way, as the entire adapter 3 is inserted deep into the accommodation part 51 of the insert trial 5 in a state in which the pressing part 33 enters the body part 31, the empty compression space 513 for compression disappears and is replaced by the adapter 3. If the front separation preventing boss 3135 is pushed to a rear portion of the separation preventing step 131 by the compression of the elastic member, the adapter 3 is completely pressed and is completely adhered to the plate trial 13. If one side of the front separation preventing boss 3135 of the second body 313 of the adapter 3 is chamfered, it may be inserted below the front separation preventing step 131 of the plate trial 13 more easily and naturally as if it was slid in the process of inserting the front separation preventing boss 3135.

Referring to FIG. 16, the force applied to the adapter 3 is removed after the adapter 3 is completely adhered to the plate trial 13, and then, the body part 31 of the adapter 3 is pushed out to the front side (in the direction of the arrow) by the restoring force of the elastic member 331. If the front separation preventing boss 3135 is completely adhered to the separation preventing step 131, the frictional force is maximized by the elastic pressing of the rear surface and the front surface, and thus the insert trial 5 and the plate trial 13 are firmly coupled to each other.

Referring to FIG. 17, it is preferable that the length of the elastic member 331 is adjusted to be large such that a force is applied to the elastic member 331 in the coupled state, and it is because the firm elastic coupling by the friction can be made possible by pressing the insert trial 5 and the plate trial 13 by the pressing part 33 and the body part 31 only when the restoring force of the elastic member 331 is present. If the initial length of the elastic member is X0, the length of the elastic member in the coupling state is X1, and the length of the elastic member in the maximum compression state in which the pressing part 33 completely enters the body part 31 is X2, (X0-X2) has to be larger than (X0-X1).

The detachment principle is the reverse order of the coupling principle, and the detachment principle of the insert trial 5 and the plate trial 13 will be described with reference to FIGS. 18, 19, and 20. FIGS. 18, 19, and 20 are cross-sectional views taken along line C-C' of FIG. 13. The cutting line starting from C goes along the center of the insert trial 5, and goes along a side surface of the insert trial 5 to an intermediate point to C'. Actually, the rear separation preventing step of the adapter 3 and the bosses 133 and 531 are not on the same plane, but it is described for the purpose of describing the operation of the adapter 3 and the operations of the rear separation preventing step and the bosses 133 and 531 in the coupling process at once.

Referring to FIG. 18, it can be identified that the insert trial 5 and the plate trial 13 are coupled to each other by the adapter 3. The front separation preventing boss 3135 is hooked by the front separation preventing step 131 to be prevented from being separated to the front side or the upper side, and the rear separation preventing boss 531 contacts the rear separation preventing step 133 to be hooked so as to be prevented from being separated to the rear side. Here, by the elastic force of the elastic member 331, the pressing part 33 presses the insert trial 5 and the body part 31 presses the plate trial 13 so that the bosses 3135 and 531 and the steps 131 and 133 are coupled to each other firmly by maximizing the frictional forces thereof.

Referring to FIG. 19, it can be seen that a pressure is applied to one side of the adapter 3 by using a hand or other tools in the direction of the arrow, and a force is applied to the elastic member 331 by the pressure and the elastic member 331 is compressed by the Hooke's Law. Accordingly, because there is no further retreatment space as the body part 31 is pushed rearwards but the pressing part 33 already contacts an end portion of the adapter accommodating part 51 of the insert trial 5, the pressing part 33 including the pressing pipe 333 enters the accommodation hole 3117a included at the rear portion 3117 of the body part 31, and the compression space 513 in the interior of the adapter accommodating part 51 that can be identified in FIGS. 14 and 18 is replaced by the adapter 3 and disappears. In this case, the front separation preventing boss 3135 also is pushed rearwards such that the contact with the front separation preventing groove 131 is released and a space for upward lifting is formed. Then, for the releasing of the contact, the length of the compression space 513 has to be larger than the length of the separation preventing groove 131.

Referring to FIG. 20, because a space for lifting the released front separation preventing boss 3135 upwards is formed in FIG. 19, a front portion of the insert trial 5 is lifted upward by applying a force upwards. If a force is applied to the front side and the insert trial 5 is pulled after the insert trial 5 is lifted by a predetermined height or more, the coupling of the rear separation preventing boss 531 and the rear separation preventing step 133 is released such that they are completely separated from each other so that the insert trial 5 and the plate trial 13 are separated from each other.

By using the coupling adapter 3, an operation of attaching and detaching the trial can be made very conveniently and promptly in total knee arthroplasty. Accordingly, the burden of the operator can be alleviated, and it is advantageous for the health of a patient through shortening of the surgery time. Further, as the process of testing the mobility of the implant can be more precise and effective by providing a function of maintaining the coupling itself firmly, it will be helpful for a surgeon to select an optimum implant.

According to another embodiment of the present disclosure, the insert trial 5 including the adapter 3 can be coupled to the plate implant as well as the plate trial 13 so that the mobility of the implant can be tested.

That is, by testing the mobility of an artificial knee joint by using a series of trials 1 and 5, it is necessary to further perform a mobility identifying operation even after a tibia coupling member implant of the corresponding size, which is determined through the operation, is implanted in the tibia of a patient when an implant having a size that is suitable for the patient is selected.

However, the artificial joint requires a high precision so as to agree with the extremely sensitive and fine structure of a human body, it may be harmful to the human body if a defect such as a slight flaw is caused in the implant which will be actually implanted in the human body and be used for a long time. For this reason, in the implants including a plate implant, the surface roughness that is the roughness of the surfaces has to be managed, and when a metallic adapter is used, a flaw may be caused due to the friction and the wear of the metallic plate implant as in the attachment and detachment process. When the implant having a flaw is implanted, it is very important to manage roughness because the roughness may influence the health of the patient. For this reason, because the plate implant having a flaw has to be replaced, it is conventionally impossible to attach the insert trial 5 to the tibia coupling member implant for a test. That is, in spite that the plate implant has the same size and the same shape as those of the plate trial 13, there exists an inconvenience in a surgical process because an identification operation using the insert trial 5 is impossible even when it is necessary to finally perform a mobility identifying operation after the plate implant is implanted due to the problem.

However, when the lower surface 3133 of the adapter 3 is made of plastic, a flaw is not generated in the adapter 3 even though the adapter 3 contacts the metallic plate implant. Accordingly, it becomes possible to finally perform a mobility identifying operation by coupling the insert trial 5 to the plate implant once again, after the tibia coupling member implant is selected to have a suitable size through a mobility test and is implanted and before the insert implant is fixed. That is, by forming the lower surface 3133 from plastic, the mobility identifying operation using the insert plate 5, to which the adapter 3 is coupled, can be performed on the plate implant as well as on the plate trial 13.

The above detailed description exemplifies the present disclosure. Furthermore, the above-mentioned contents describe the exemplary embodiment of the present disclosure, and the present disclosure may be used in various other combinations, changes, and environments. That is, the present disclosure can be modified and corrected without departing from the scope of the present disclosure that is disclosed in the specification, the equivalent scope to the written disclosures, and/or the technical or knowledge range of those skilled in the art. The written embodiment describes the best state for implementing the technical spirit of the present disclosure, and various changes required in the detailed application fields and purposes of the present disclosure can be made. Accordingly, the detailed description of the present disclosure is not intended to restrict the present invention in the disclosed embodiment state. Furthermore, it should be construed that the attached claims include other embodiments.

What is claimed is:

1. A knee trial that is coupled to identify the mobility of an implant before the implant is implanted by total knee arthroplasty, the knee trial comprising:
    a plate trial;
    an insert trial; and
    an adapter for attaching and detaching the plate trial and the insert trial, the adapter comprising a body part and a pressing part, the pressing part having an elastic member, the body part and the pressing part being coupled to each other so as to be movable with respect to each other,
    wherein the pressing part comprises a pressing pipe having an insertion hole in which the elastic member is accommodated, one end of the elastic member being supported by the body part and an opposite end of the elastic member being supported by the pressing pipe,
    wherein the adapter is movable between a first position where the plate trial and the insert trial are securely held together and a second position where the plate trial is freely removable from the insert trial.

2. The knee trial of claim 1, wherein the body part comprises a wing that is slid and guided with respect to the insert trial such that the adapter is slid with respect to the insert trial.

3. The knee trial of claim 1, wherein the pressing pipe comprises a slot that is guided by the body part to be movable while being elastically pressed or restored in a forward/rearward direction in a state in which the pressing pipe is coupled to the body part.

4. The knee trial of claim 3, wherein the body part of the adapter comprises a front separation preventing boss for firm coupling to the plate trial, on one side thereof, and
    the plate trial comprises a front separation preventing step contacting the front separation preventing boss of the adapter, on one side thereof, such that the adapter is prevented from being separated from the plate trial.

5. The knee trial of claim 4, wherein one side of the front separation preventing boss is chamfered to be easily coupled and released when being attached to and detached from the plate trial.

6. The knee trial of claim 4, wherein the insert trial comprises a rear separation preventing boss for firm coupling to the plate trial, on a rear surface thereof, and
    the plate trial comprises a rear separation preventing step contacting the separation preventing boss of the insert trial, on a rear surface thereof, such that the insert trial is firmly coupled to the plate trial and is prevented from being separated.

7. The knee trial of claim 1, wherein an upper end of a front surface of the body part, which contacts the insert trial, is chamfered inwards to have an inclination that is identical to an oblique line portion of the insert trial.

8. A knee trial that is coupled to identify the mobility of an implant before the implant is implanted by total knee arthroplasty, the knee trial comprising:
    a plate trial;
    an insert trial; and an adapter for attaching and detaching the plate trial and the insert trial, the adapter comprising a body part and a pressing part, the pressing part having an elastic member, the body part and the pressing part being coupled to each other so as to be movable with respect to each other, at least a portion of a contact surface of the body part of the adapter, which contacts the plate trial, is formed of plastic, wherein the body part comprises a first body part and a second body part, the first body part and the second body part being coupled together by a fastening member, wherein the adapter is movable between a first position where the plate trial and the insert trial are securely held together and a second position where the plate trial is freely removable from the insert trial.

9. The knee trial of claim 8, wherein the second body part is formed of plastic.

* * * * *